Figure 1:

United States Patent [19]

Adolf et al.

[11] Patent Number: 5,916,561
[45] Date of Patent: Jun. 29, 1999

[54] MONOCLONAL ANTIBODY AGAINST CD44V6

[75] Inventors: Günther R. Adolf, Vienna; Erik Patzelt, Punkersdorf, both of Austria

[73] Assignee: Boehringer Ingelheim International GmbH, Germany

[21] Appl. No.: 08/750,359

[22] PCT Filed: Jun. 2, 1995

[86] PCT No.: PCT/EP95/02126

§ 371 Date: Feb. 12, 1997

§ 102(e) Date: Feb. 12, 1997

[87] PCT Pub. No.: WO95/33771

PCT Pub. Date: Dec. 14, 1995

[30] Foreign Application Priority Data

Jun. 8, 1994 [DE] Germany ............................. 44 19 913
Sep. 2, 1994 [DE] Germany ............................. 44 31 297

[51] Int. Cl.$^6$ .......................... A61K 39/395; C12N 5/12; G01N 33/574; C07K 16/28
[52] U.S. Cl. ..................... 424/178.1; 424/181.1; 424/133.1; 424/174.1; 424/141.1; 424/143.1; 424/144.1; 435/346; 435/330; 435/344.1; 435/7.23; 530/388.2; 530/388.23; 530/388.85
[58] Field of Search ............................. 530/388.2, 388.23, 530/388.85; 424/181.1, 178.1, 133.1, 174.1, 141.1, 143.1, 144.1; 435/346, 330, 344.1, 7.23

[56] References Cited

FOREIGN PATENT DOCUMENTS

WO 94/12631 6/1994 WIPO.
WO 95/00658 1/1995 WIPO.
WO 95/00851 1/1995 WIPO.

OTHER PUBLICATIONS

Salmi, Marko et al., in Journal of Cell Biol. vol. 122: 431–442, Jul. 1993. (see *1449).

Heider, Karl–Heinz et al., "Differential Expression of CD44 Splice Variants in Intestinal–and Diffuse–Type Human Gastric Carcinomas and Normal Gastric Mucosa," Cancer Research 53, 4197–4203, Sep. 15, 1993.

Jackson, D.G., et al., "Expression of Alternatively Spliced Forms of the CD44 Extracellular–Matrix Receptor on Human Lung Carcinomas," Int. J. Cancer: Supplement 8, 110–115 (1994).

Kreitman, Robert J., et al., "Pseudomonas Exotoxin–based Immunotoxins Containing the Antibody LL2 or LL2–Fab' Induce Regression of Subcutaneous Human B–Cell Lymphoma in Mice," Cancer Research 53, 819–825, Feb. 15, 1993.

Salmi Marko, et al., "Expression of Domain 3 Containing Isoforms of CD44 in Man," 8th International Congress of Immunology, p. 274, abstract W–47/I–34 (1992).

Salmi, Marko, et al., "Regulated Expression of Exon v6 Containing Isoforms of CD44 in Man: Downregulation During Malignant Transformation of Tumors of Squamocellular Origin," The Journal of Cell Biology, vol. 122, No. 2, 431–442, Jul. 1993.

Wielenga, Vera J.M., et al., "Expression of CD44 Variant Proteins in Human Colorectal Cancer Is Related to Tumor Progression," Cancer Research 53, 4754–4756, Oct. 15, 1993.

Primary Examiner—Toni R. Scheiner
Assistant Examiner—Geetha P. Bansal
Attorney, Agent, or Firm—Finnegan, Henderson Farabow, Garrett & Dunner, L.L.P.

[57] ABSTRACT

The invention concerns an antibody active against an epitope coded by the exon v6 variant of the CD44 gene. The antibody concerned has characteristics superior to those of prior art antibodies and is suitable for use in therapy and diagnosis.

17 Claims, 6 Drawing Sheets

```
         *  *  *****  *****  **  *  *        **  ****  *  **
Rat:     WADPNSTTEEAATQKEKWFENEWQGKNPPTPSEDSHVTEGT T
Human:   QATPSSTTEETATQKEQWFGNRWHEGYRQTPREDSHSTTGTAA
```

Peptide Ra1 or Hu1, resp.

*Fig. 2*

MONOCLONAL ANTIBODY AGAINST CD44V6

The invention relates to a monoclonal antibody against an epitope which is coded by the variant exon v6 of the CD44 gene, antibody molecules derived therefrom and uses of the antibody or antibody molecules for diagnostic and therapeutic purposes.

Recently it has been shown that the expression of variants of the surface glycoprotein CD44 is necessary and sufficient for causing so-called spontaneous metastatic behaviour of a non-metastasizing rat pancreatic adenocarcinoma cell line as well as a non-metastasizing rat fibrosarcoma cell line (Günthert et al., 1991). While the smallest CD44 isoform, the standard form CD44s (or CD44std), is ubiquitously expressed in different tissues including epithelial cells, certain CD44splice variants (CD44v, CD44var) are expressed only in a subset of epithelial cells. The CD44variants are generated by alternative splicing in a way that the sequences of ten exons (v1–v10) are completely excised in CD44s but can appear in the bigger variants in different combinations (Screaton et al., 1992; Tölg et al., 1993; Hofmann et al., 1991). The variants differ in that different amino acid sequences are inserted at a certain site of the extracellular part of the protein. Such variants can be detected in various human tumor cells as well as in human tumor tissue. So, the expression of CD44 variants in the course of colorectal carcinogenesis has recently been investigated (Heider et al., 1993a). The expression of CD44variants is absent in normal human colon epithelium, and only a weak expression is detectable in the proliferating cells of the crypts. In later stages of the tumor progression, e.g. in adenocarcinomas, all malignancies express variants of CD44. Tissue expression of variant CD44 on a high level has also been shown in aggressive Non-Hodgkin lymphomas (Koopman et al., 1993).

Exon v6 appears to play a special role especially in the course of metastatic spread, (Rudy et al., 1993). In an animal model, antibodies against v6 specific epitopes could prevent the settlement of metastatic cells and the growth of metastases (Seiter et al., 1993). In colon carcinomas, v6 expression correlates with tumor progression (Wielenga et al., 1993). In gastric carcinomas, v6 expression is an important diagnostic marker to distinguish tumors of the intestinal type from those of the diffuse type (Heider et al., 1993b). In the latter two publications, v6 expression has been determined using antibodies against v6 specific epitopes.

Monoclonal antibodies against epitopes coded by exon v6 are known in the state of the art (Hofmann et al., 1991; Wielenga et al., 1993). Because of the high potential utility such antibodies could have in diagnosis and therapy, there is a great need of antibodies with improved properties.

The present invention has the object of providing an antibody with significantly better properties as compared to the known v6 specific antibodies.

The present invention has succeeded in this aim. It relates to an antibody with the designation VFF-18. The invention further relates to a hybridoma cell line which secretes this antibody and has been deposited on Jun. 7, 1994 under the accession number DSM ACC 2174 with the DSM-Deutsche Sammlung für Mikroorganismen und Zellkulturen GmbH, Mascheroder Weg 1b, D-38124 Braunschweig, Germany.

The terms "antibody" or "antibody molecules" hereinafter refer not only to complete immunoglobulins but also equivalent substances with regard to binding specificity and affinity as well as the antibody derivatives and recombinant antibody molecules described.

The antibody VFF-18 has been prepared by a process according to example 1. The antibody can also be obtained from the hybridoma cell line deposited. It is within the skills of the average artisan to prepare derivatives of the antibody of the invention or, starting from a sequence analysis of the antibody and/or by use of the hybridoma cell line producing this antibody, to prepare recombinant antibody molecules with the same idiotype, i.e. antibody molecules having the same amino acid sequence in the region of the antigen binding site (complementarity-determining regions, CDR) as the antibody VFF-18. Such derivatives as well as recombinant antibody molecules are therefore explicitly included in the present invention.

For example, Fab or F(ab')$_2$ fragments or other fragments could be generated from the complete immnunoglobulin of the VFF-18 antibody (Kreitman et al., 1993). For diagnostic procedures, VFF-18 antibody molecules, fragments thereof, or recombinant antibody molecules with the same idiotype, for example, could be linked to radioactive isotopes like $^{131}$I, $^{111}$In, $^{99m}$Tc or radioactive compounds (Larson et al., 1991; Thomas et al., 1989; Srivastava, 1988), enzymes like peroxidase or alkaline phosphatase (Catty et Raykundalia, 1989), fluorescence dyes (Johnson, 1989), or biotin molecules (Guesdon et al., 1979). For therapeutic applications, VFF-18 or VFF-18-derived antibody molecules could be linked to toxins (Vitetta et al., 1991; Vitetta et Thorpe, 1991; Kreitman et al., 1993; Theuer et al., 1993), cytostatics (Schrappe et al., 1992), prodrugs (Wang et al., 1992; Senter et al., 1989) or radioactive substances. Furthermore, the antibody could be linked to a cytokine or an immunomodulatory polypeptide, for example tumor necrosis factor or interleukin-2.

Furthermore, after analysis of the amino acid sequence of the antibody VFF-18 and/or by use of the hybridoma cell line producing this antibody, especially by the analysis of the genetic information contained within these cells, the skilled person is able to produce recombinant antibody molecules with the same idiotype as VFF-18. Methods to achieve this form part of the state of the art. For example, such recombinant antibodies could be humanised antibodies (Shin et al., 1989; Guissow et Seemann, 1991), bispecific antibodies (Weiner et al., 1993; Goodwin, 1989), single chain antibodies (scFv, Johnson et Bird, 1991), complete or fragmentary immunoglobulins (Coloma et al., 1992; Nesbit et al., 1992; Barbas et al., 1992), or antibodies generated by chain shuffling (Winter et al., 1994). Humanised antibodies may be produced, for example, by CDR grafting (EP 0239400). Framework regions may also be modified (EP 0519596). To humanise antibodies, methods such as PCR (cf. for example EP 0368684; EP 0438310; WO 9207075) or computer modelling (cf. for example WO 9222653) may be used nowadays. Fusion proteins, e.g. single chain antibody/toxin fusion proteins (Chaudhary et al., 1990; Friedman et al., 1993) may also be produced. Antibody molecules of this kind are therefore also included in the invention.

It is further within the skills of the average skilled man to identify the exact epitope of VFF-18 and, with this knowledge, to produce equivalent antibodies with the same binding specifity. The exact epitope may be identified by peptide binding studies as in example 2, e.g. by varying the sequence of the peptide Hul. Therefore, such antibodies are also within the scope of the present invention.

A further aspect of the present invention is the use of VFF-18 or VFF-18 derived or equivalent antibody molecules for diagnosis and therapy.

Diagnostic processes can be based on known procedures using the antibody molecules of the present invention, for example enzyme-linked imnuunoassays (ELISA, Catty et Raykundalia, 1989), radioimmunoassays (Catty et Murphy, 1989), immunohistochemical methods (Heider et al., 1993b), or western blots. Appropriately, such procedures can be performed with tissue samples or liquids obtained from the body, for example by way of biopsy. Such analyses can be done qualitatively, semi-quantitatively, or quantitatively. The antibody or antibody molecules may be used as described in the prior art for other v6-specific antibodies (WO 9500851), the beneficial qualities of the antibody or antibody molecules according to the invention constituting a significant improvement to such processes.

Apart from in vitro diagnosis, the antibody molecules according to the invention are also suitable for in vivo diagnosis, especially of tumours. If the antibody molecule bears a detectable label, the label may be detected for diagnostic purposes, e.g. for imaging the tumour in vivo or for radioguided surgery, for example. For use of antibodies combined with radioactive isotopes for immune scintigraphy (imaging), for example, there are a number of procedures by means of which the invention may be put into practice (Siccardi et al., 1989; Keenan et al., 1987; Perkins and Pimm, 1992; Colcher et al., 1987; Thompson et al., 1984).

A therapeutic application can be performed e.g. analogously to the use of the antibody ASML1.1 (Seiter et al., 1993). The antibody molecule can be applied systemically or topically, for example by intravenous (bolus or permant infusion), intraperitoneal, intramusculary, or subcutaneous injection or infusion. Also, single organs or extremities can be perfused. Protocols for the application of conjugated or non-conjugated antibodies (complete immunoglobulins, fragments, recombinant chimeric molecules, or the like) can be found within the art (Mulshine et al., 1991; Larson et al., 1991; Vitetta et Thorpe, 1991; Vitetta et al., 1991; Breitz et al., 1992; Press et al., 1989; Weiner et al., 1989; Chatal et al., 1989; Sears et al., 1982).

The superior properties of VFF-18 as compared to other anti-CD44v6 antibodies are demonstrated by the examples 2 to 4.

FIGURES

FIG. 1: Schematic representation of the GST-CD44 (v3–v10) fusion protein. GST=glutathione-S-transferase of *Schistosoma japonicum*. v3–v10=variant inserts of keratinocytic CD44. The arrow marks a thrombin cleavage site.

FIG. 2: Sequence comparison of the exon v6 of the CD44 gene of man and rat. The sequences of the peptides Ral and Hu1 recognized by the antibodies 1.1ASML (anti-rat CD44v6 ) or VFF-18 (anti-human CD44v6 ), respectively, are bold-faced. Identical amino acids are marked by asterisks.

Figure 3A:
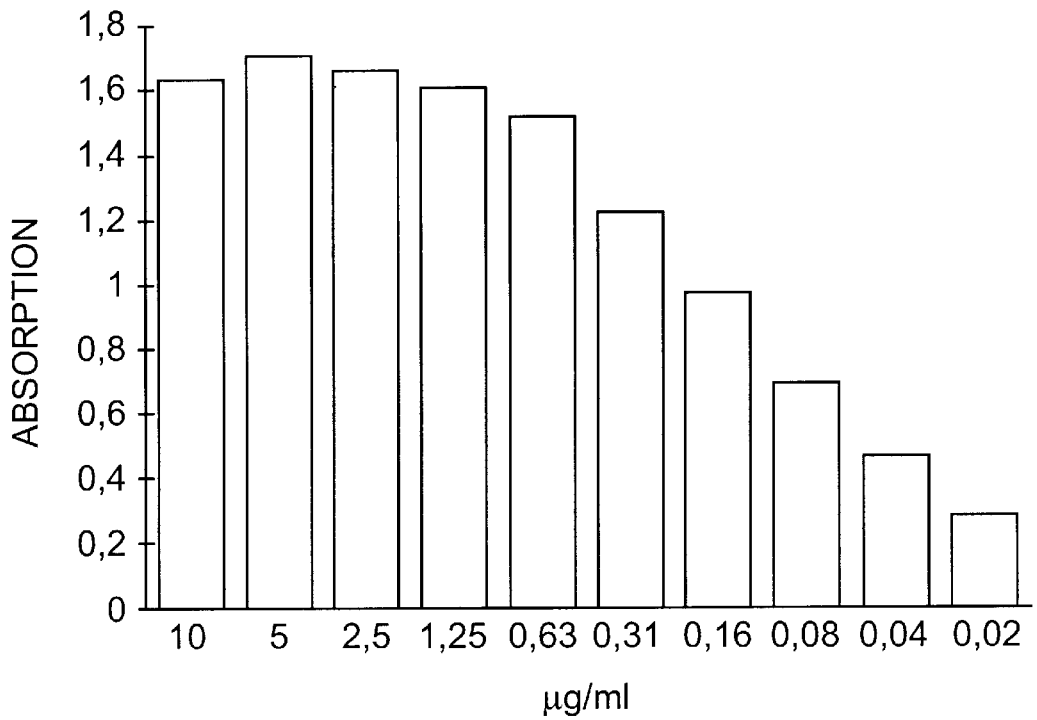
Figure 3B:
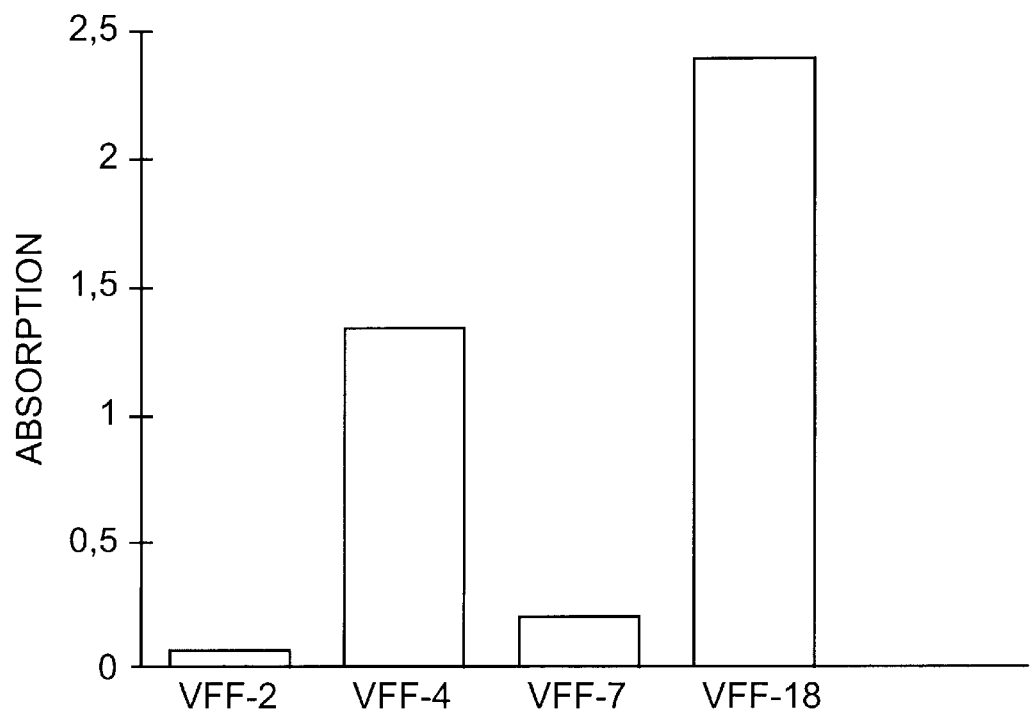
Figure 3C:
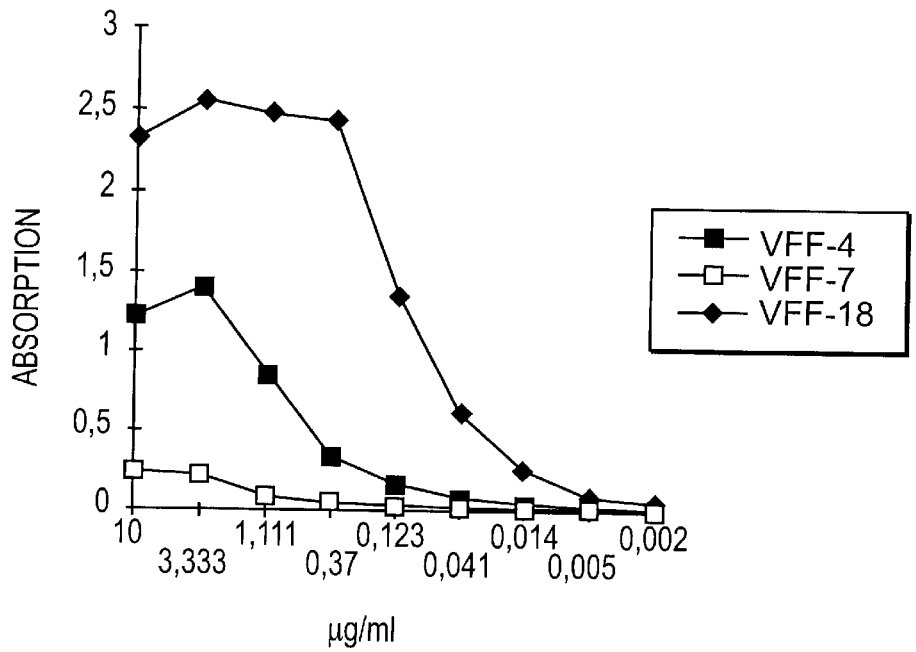

FIG. 3: Binding of CD44v6 specific antibodies to synthetic peptides. The binding of the antibodies to the peptides was determined by an ELISA, the peptides being immobilised and then incubated with antibody solutions. After appropriate washing steps, bound antibody was detected by peroxidase-conjugated anti-mouse IgG antibody. (A): In a first experiment, the binding of a rat specific CD44v6 antibody, 1.1ASML, to the peptide Ral (KWFEN EWQGK NPPT) was demonstrated. (B): In a further experiment, a peptide homologous to Ral but derived from the human CD44v6 sequence was synthesized. Different anti-human CD44v6 hybridoma supernatants were bound to this peptide called Hu1 (QWFGN RWHEG YRQT). It was found that VFF-18 bound to the peptide much better than the other antibodies tested. (C): For a quantitative evaluation, the experiment was repeated with different concentrations of purified antibodies. Also in this experiment, it could be seen that VFF-18 showed a higher binding affinity as compared to the other antibodies.

Figure 4:
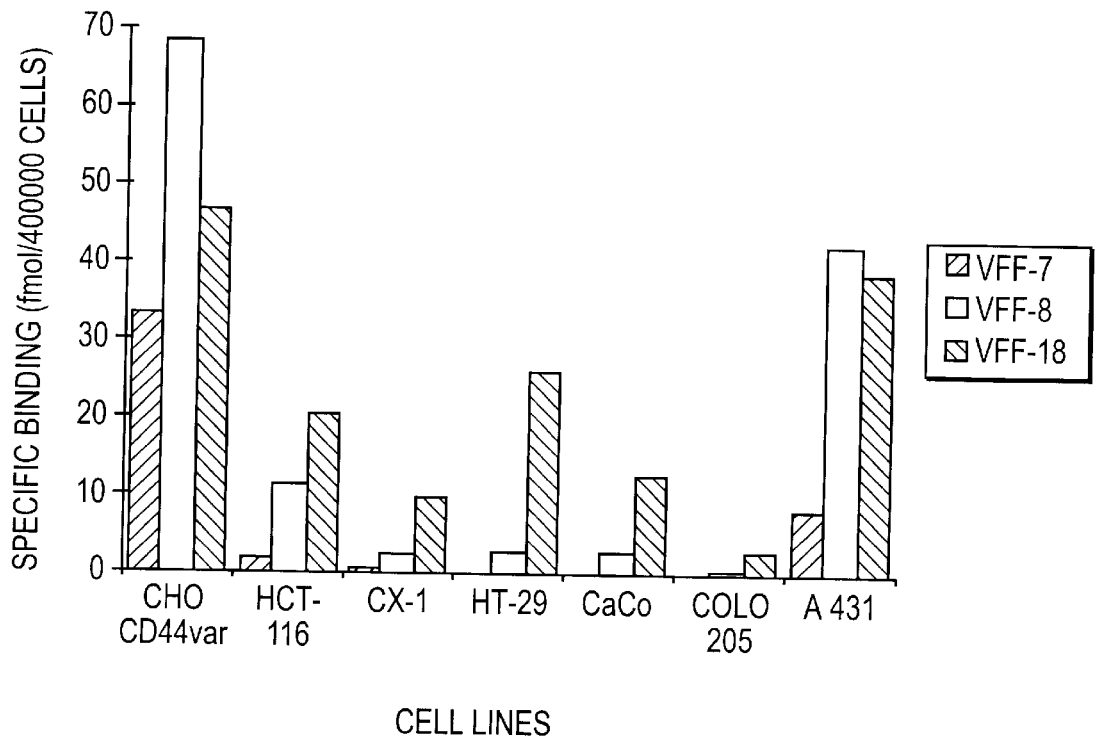

FIG. 4: Binding of radioactive antibody to tumor cells. The 3 antibodies VFF-7 (anti-v6 ), VFF-8 (anti-v5), and VFF-18 (anti-v6 ) were radioactively labeled with N-succinimyl[2,3-$^3$H]propionate and used for binding assays with different tumor cell lines. The following cell lines were used: CHO-CD44var: recombinant hamster cell line (Chinese hamster ovary) expressing human variant CD44 (exons v3–v10) on the cell surface; HCT-116, CX-1, HT-29, CaCo, COLO 205: human colon carcinoma cell lines; A431: human squameous cell carcinoma line. The specific binding of the antibodies to the different cell lines is shown. While the binding of the v6 specific antibodies VFF-7 and VFF-18 to the recombinant cell line CHO-CD44var is of the same magnitude, the antibodies show very different binding behaviour with respect to the tumor cell lines. In some cases, only VFF-18 and, to a lesser extent, VFF-8 binding can be seen (HT-29, CaCo, COLO 205), while in other cases VFF-18 binds remarkably better than VFF-7.

Figure 5A:
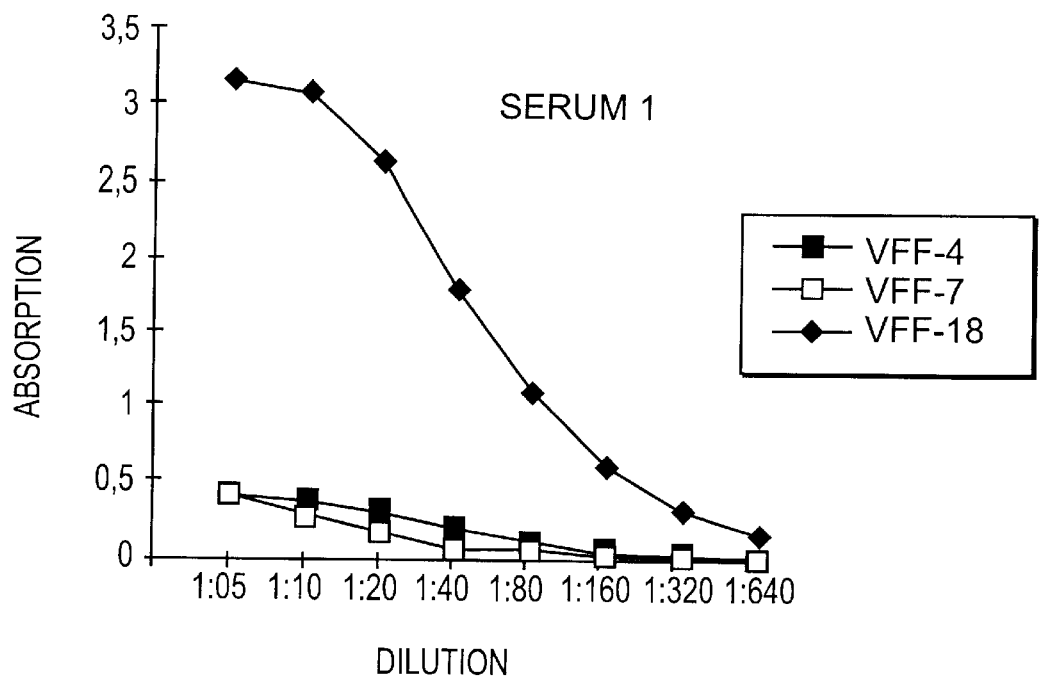
Figure 5B:
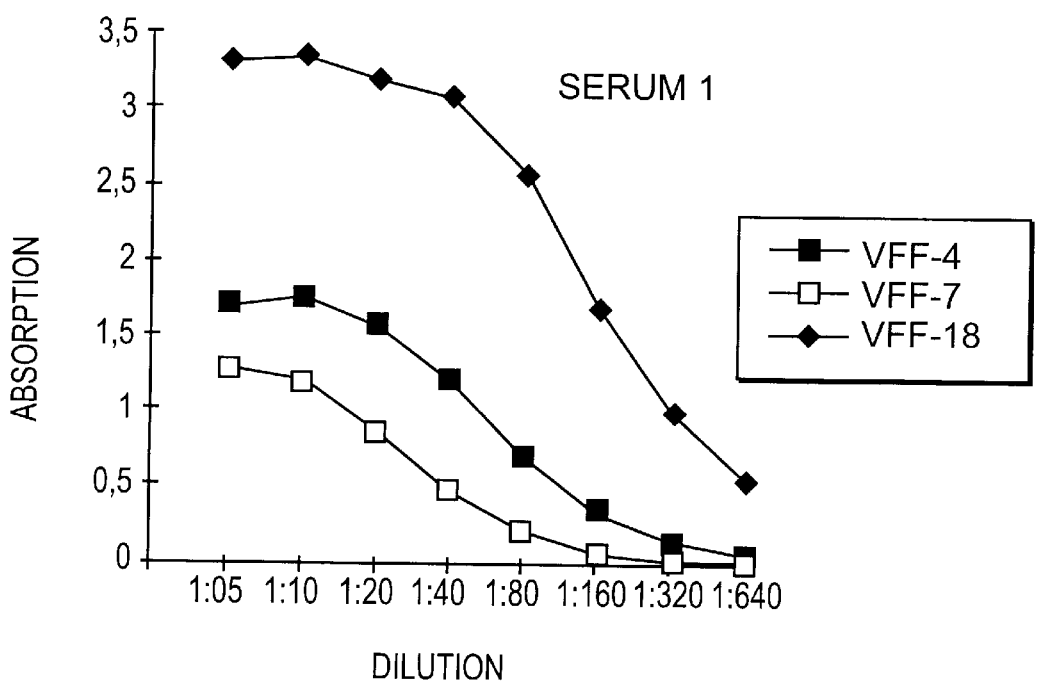

FIG. 5: Detection of soluble CD44variants containing exon v6 in normal human serum. The 3 v6 specific antibodies VFF-4, VFF-7, and VFF-18, respectively, were used as coating antibodies in a sandwich ELISA. In all three cases, a peroxidase-linked CD44std specific antibody (BU-52, std=standard) was used as detection antibody. The signal of two different normal human sera at different dilutions is shown in these assays ((A) and (B)). In both cases, a substantial stronger signal is observed with VFF-18 as compared to the two other antibodies.

Figure 6:
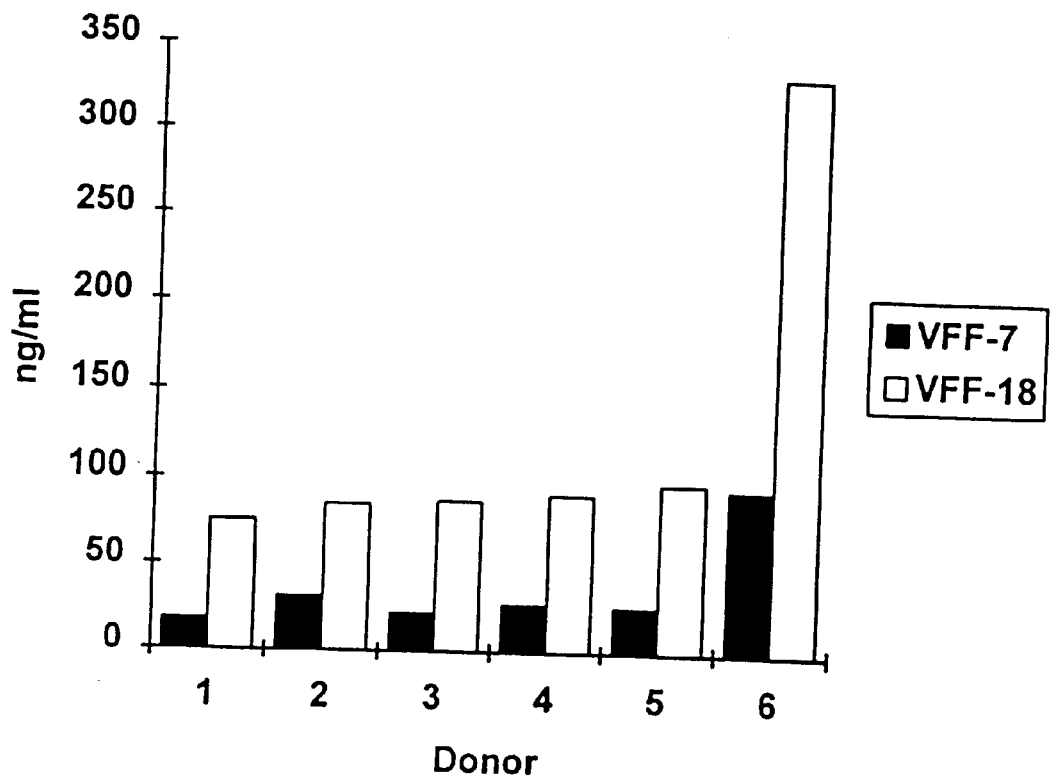

FIG. 6: Serum levels of CD44variants containing v6 . The content of soluble CD44var in sera of 6 healthy donors was determined by two different ELISAs. In one test VFF-7 was used, while in the other VFF-18 was used as coating antibody. Both antibodies recognize exon v6 . In both cases, a recombinant soluble CD44variant (exon v3–v10) produced in CHO cells served as control. In the average, the VFF-18 ELISA showed 3.5 times higher values as compared to the VFF-7 ELISA. This means that the soluble CD44var occurring in serum is better recognized by VFF-18 than by VFF-7.

EXAMPLES

Example 1

Production of the Monoclonal Antibody VFF-18

Cloning of pGEX Fusion Proteins

The complete variant region of the HPKII type of CD44v (Hofmann et al., 1991) was amplified by polymerase chain reaction (PCR) from human keratinocyte cDNA. The two PCR primers which were used (5'-CAGGCTGGGAGCCAAATGAAGAAAATG-3', positions 25–52, and 5'-TGATAAGGAACGATTGACATT AGAGTTGGA-3', positions 1013-984 of the LCLC97 variant region, as described by Hofmann et al), contained an EcoRI-recognition site which was used to clone the PCR product directly into the vector pGEX-2T (Smith et al., 1988). The resulting construct (PGEX CD44v HPKII, v3–v10) codes for a fusion protein of about 70 kdal, consisting of glutathione-S-transferase of *Schistosoma japonicum* and the exons v3–v10 of human CD44 (FIG. 1; Heider et al., 1993a). The fusion protein was expressed in *E. coli* and subsequently purified by affinity chromatography on glutathione agarose (Smith et al., 1988).

Immunisation and Screening

Female Balb/c mice were immunised intraperitoneally with the affinity purified fusion protein according to the following scheme:

1. Immunisation: 90 g of fusion protein in complete Freund's adjuvant
2. and 3. Immunisation: 50 g of fusion protein in incomplete Freund's adjuvant.

The immmnisations were done at intervals of 4 weeks, respectively. 14 days after the last immunisation, the animals were additionally immunised with 10 µg of fusion protein in phosphate buffered saline (PBS) at the time for three successive days. The following day, spleen cells of an animal with a high antibody titer were fused with P3.X63-Ag8.653 murine myeloma cells using polyethylene glycol 4000. Hybridoma cells were selected in microtiter plates in HAT medium (Köhler et Milstein, 1975. Kearney et al., 1979).

The determination of the antibody titer in serum or the screening of the hybridoma supernatant, respectively, were carried out using an ELISA. In this assay, microtiter plates were coated with fusion protein (GST-CD44v3–10) or with glutathione-S-transferase first. Then, the wells were incubated with serial dilutions of serum samples or hybridoma supernatants, and the specific antibodies were detected by peroxidase-coupled antibodies against mouse immunoglobulin. Hybridomas reacting with glutathione-S-transferase only were discarded. The remaining antibodies were then characterized using domain specific fusion proteins (exon v3, exon v5+v6, exon v6+v7, exon v8–v10) (Koopman et al., 1993). Afterwards, the immunnhistochemical reactivity of these antibodies was tested on human skin sections. The antibody VFF-18 was then identified by binding to the synthetic peptide Hul (QWFGN RWHEG YRQT). The sequence of Hul is a fragment of the human CD44 exon v6.

Example 2

Binding of CD44v6 Specific Antibodies to Synthetic Peptides

The binding of CD44v6 specific antibodies to synthetic peptides was determined by use of an ELISA.
Solutions:

Coating buffer: 0.05 M sodium carbonate, pH 9.6

Assay buffer: PBS (phosphate buffered saline) 0.5% BSA (bovine serum albumin) 0.05% Tween 20 substrate solution: Kierkegaard & Perry Laboratories, Gaithersburg Md., USA; TMB peroxidase substrate: peroxidase solution B ($H_2O_2$) 1:1

The peptides (50 µg/ml in coating buffer) were immobilised on NUNC Maxisorp immunoplates (1.1ASML) or Acti A plates from Bio Products (VFF antibodies) at 4° C. overnight. In the case of the Acti A plates, the peptide is bound covalently to the plate. Then, the plates were washed with PBS/0.05% Tween 20, free adsorption sites on the plate surface were blocked using assay buffer (1 hour at room temperature) and then washed again with PB5/0.05% Tween 20 . . . Acti A plates were reduced by 10 mM sodium boron hydride in 20 mM sodium hydrogen carbonate, pH 9.0, (1 hour shaking at room temperature) and then washed three times. Then, hybridoma supernatants or antibody solutions in assay buffer, respectively, in concentrations between 0.02 and 10.0 µg/ml were added to the wells and shaked for two hours at room temperature. Afterwards, the plates were washed three times with PBS/0.05% Tween 20. Then, 100 µl/well horseradish peroxidase conjugated anti-mouse IgG antibody in an appropriate dilution in assay buffer were added. After two hours of incubation at room temperature on a shaker, the plates were washed three times and substrate solution was added to the wells. After 10–15 minutes, the development was stopped with 2 M sulfuric acid, and the absorption was measured at 450 nm (reference 690 nm) in a photometer.

In a first experiment, the binding of the rat CD44v6 specific antibody 1.1ASML to the peptide Ral (KWFEN EWQGK NPPT) was detected (Table 1, FIG. 3 (A)).

TABLE 1

| 1.1 ASML g/ml | Absorption |
|---|---|
| 10.00 | 1.652 |
| 5.00 | 1.702 |
| 2.50 | 1.658 |
| 1.25 | 1.595 |
| 0.63 | 1.502 |
| 0.31 | 1.211 |
| 0.16 | 0.971 |
| 0.08 | 0.686 |
| 0.04 | 0.458 |
| 0.02 | 0.270 |

In a further experiment, a peptide derived from the human CD44v6 sequence homologous to Ral was synthesized (Hul, QWFGN RWHEG YRQT). Different anti-human CD44v6 antibodies were bound to Hul. Suprisingly, it was found that VFF-18 showed a much higher binding affinity to this peptide as compared to the other antibodies tested (Table 2, FIG. 3 (B)).

TABLE 2

| Antibody | Absorption |
|---|---|
| VFF-2 | 0.067 |
| VFF-4 | 1.333 |
| VFF-7 | 0.199 |
| VFF-18 | 2.384 |

For a quantitative evaluation, purified anti-human CD44v6 antibodies at various concentrations were bound to the peptide Hul. Here, too, the substantially better binding affinity of VFF-18 as compared to the other antibodies can be seen (Table 3, FIG. 3 (C)).

TABLE 3

| µg/ml Antibody | VFF-4 | VFF-7 | VFF-18 |
|---|---|---|---|
| 10.000 | 1.225 | 0.247 | 2.320 |
| 3.333 | 1.404 | 0.226 | 2.550 |
| 1.111 | 0.853 | 0.094 | 2.483 |
| 0.370 | 0.336 | 0.054 | 2.426 |
| 0.123 | 0.163 | 0.028 | 1.354 |
| 0.041 | 0.086 | 0.025 | 0.615 |
| 0.014 | 0.048 | 0.021 | 0.266 |
| 0.005 | 0.036 | 0.031 | 0.095 |
| 0.002 | 0.021 | 0.021 | 0.061 |

Example 3

Binding of Radioactively Labeled CD44v6 Specific Antibodies to Tumor Cell Lines

Radioactive Labeling of Antibodies 1 mCi N-succinimidyl-[2,3-$^3$H]-propionate ([$^3$H]-NSP, Amersham, 1 mCi/mi) were evaporated in a siliconized sample vessel at 0° C. in a water jet vacuum nearly till dryness. 15 μg antibody (1 mg/ml in PBS, pH 7.4) were added and incubated for 48 hours at 4° C. Subsequently, excessive [³H]-NSP was quenched by reaction with 30 μl 1 M glycine in PBS for 20 minutes at room temperature. The separation of the labeled antibody from [³H]-glycine was carried out using a Sephadex G-25-M column (column volume 15 ml) and PBS/0.5% BSA as elution buffer. The [³H]-labeled antibody appears in the void volume. The amount of antibody was determined using an ELISA for the detection of mouse immunoglobulin, and the specific activity was calculated.

Binding of Radiolabeled Antibodies to Tumor Cells

The 3 antibodies VFF-7 (anti-v6 ), VFF-8 (anti-v5), and VFF-18 (anti-v6 ) were radioactively labeled with N-succinimidyl-[2,3-³H]propionate and used for binding assays with different tumor cell lines. The following cell lines were used: CHO-CD44var: -recombinant hamster cell line (Chinese hamster ovary) expressing human variant CD44 (exons v3–v10) on the cell surface; HCT-116, CX-1, HT-29, CaCo, COLO 205: human colon carcinoma cell lines; A431: human squameous cell carcinoma line.

The cells were seeded in 12-well tissue culture plates and incubated overnight at 37° C. in a $CO_2$ incubator, washed once with PBS and fixed with ethanol (1 minute at room temperature). Then they were washed once with culture medium (RPMI 1640/10% fetal calf serum) and the radioactive antibody was added (250 000 dpm/well in culture medium). After incubation of 25 hours at room temperature on a shaker, the plates were washed three times with PBS/0.5% BSA, the cells were solubilised with 0.1 M NaOH/1% Triton X-100, and the radioactivity was measured in a scintillation counter. Unspecific binding was determined in the presence of a 100 fold excess of unlabeled antibody. The binding was related to a standardized cell number (400 000 cells). After determination of the specific activity of the antibodies, the amount of bound antibody can be expressed in fmol.

Table 4 and FIG. 4 show the specific binding of the antibody to various cell lines. While the binding of the v6 specific antibodies VFF-7 and VFF-18 to the recombinant cell line CHO-CD44var is of approximately the same magnitude, the antibodies show substantially different binding behaviour with respect to the tumor cell lines. In some cases, only VFF-18 and, to a lesser extent, VFF-8 binding can be seen (HT-29, CaCo, COLO 205), while in other cases VFF-18 binds remarkably better than VFF-7.

TABLE 4

| Cell line | VFF-7 fmol | VFF-8 fmol | VFF-18 fmol |
|---|---|---|---|
| CHO CD44var | 33.50 | 68.42 | 46.52 |
| HCT-116 | 1.44 | 11.08 | 20.22 |
| CX-1 | 0.19 | 2.20 | 9.48 |
| HT-29 | 0.00 | 2.60 | 26.07 |
| CaCo | 0.03 | 2.81 | 12.57 |
| COLO 205 | 0.00 | 0.32 | 2.88 |
| A431 | 8.19 | 42.32 | 38.73 |

Example 4

ELISA for the Determination of Soluble CD44v6 in Serum

Solutions:
Coating buffer: 0.05 M Sodium carbonate, pH 9.6

Assay buffer: PBS (phosphate buffered saline 0.5% BSA (bovine serum albumin) 0.05% Tween 20

Sample diluent: Bender MedSystems, Vienna, Austria

Substrate solution: Kierkegaard & Perry Laboratories, Gaithersburg Md., USA; TMB peroxidase substrate: peroxidase solution B ($H_2O_2$) 1:1

Microtiter plates (Nunc-Immunoplate MaxiSorp F96) were coated with 5 μg/ml of a CD44v6 specific antibody (incubation at 4° C. overnight). Subsequently, the plates were washed with PBS/0.05% Tween 20, free adsorption sites on the surface of the plates were blocked using assay buffer (1 hour at room temperature), and plates were washed again. Serum samples were prediluted at least 1:5 in sample diluent and further diluted serially 1:2 in the wells. Then, 50 μl/well horseradish peroxidase conjugated anti-CD44std antibody (Clone BU-52, The Binding Site, Birmingham) were added in an appropriate dilution (1:3000–1:10000) in assay buffer. After three hours of incubation on a shaker at room temperature, plates were washed three times, and substrate solution was added. After 10 to 15 minutes, development was stopped with 2 M sulfuric acid, and the absorption was measured at 450 nm (reference 690 mn) in a photometer.

For quantification, a serial dilution of a soluble CD44standard sample in assay buffer was prepared in parallel to the serum samples. This preparation was purified from a supernatant of recombinant hamster cells (CHO) expressing soluble CD44v3–v10. CD44v3–v10 is a human CD44variant containing the exons v3 to v10 .

Table 5 and FIG. 5 demonstrate the presence of soluble CD44variants containing exon v6 in normal human serum. The 3 v6 specific antibodies VFF-4, VFF-7, and VFF-18, respectively, were used as coating antibodies in a sandwich ELISA. In all three cases, a peroxidase-linked CD44std specific antibody (BU-52, std=standard) was used as detection antibody. The signal of two different normal human sera at different dilutions is shown ((A) and (B)). In both cases, a substantial stronger signal is observed with VFF-18 as compared to the two other antibodies.

TABLE 5 A

| | Serum 1 | | |
|---|---|---|---|
| Dilution | VFF-4 | VFF-7 | VFF-18 |
| 1:5 | 0.406 | 0.417 | 3.143 |
| 1:10 | 0.378 | 0.289 | 3.055 |
| 1:20 | 0.296 | 0.179 | 2.630 |
| 1:40 | 0.207 | 0.072 | 1.778 |
| 1:80 | 0.109 | 0.062 | 1.084 |
| 1:160 | 0.050 | 0.030 | 0.594 |
| 1:320 | 0.026 | 0.008 | 0.318 |
| 1:640 | 0.012 | 0.007 | 0.159 |

TABLE 5 B

| | Serum 2 | | |
|---|---|---|---|
| Dilution | VFF-4 | VFF-7 | VFF-18 |
| 1:5 | 1.690 | 1.280 | 3.290 |
| 1:10 | 1.756 | 1.185 | 3.321 |
| 1:20 | 1.564 | 0.857 | 3.163 |
| 1:40 | 1.213 | 0.468 | 3.050 |
| 1:80 | 0.699 | 0.208 | 2.537 |
| 1:160 | 0.336 | 0.061 | 1.666 |

TABLE 5 B-continued

| | Serum 2 | | |
|---|---|---|---|
| Dilution | VFF-4 | VFF-7 | VFF-18 |
| 1:320 | 0.138 | 0.014 | 0.988 |
| 1:640 | 0.054 | 0.018 | 0.546 |

Table 6 and FIG. 6 show serum levels of v6 containing CD44variants. The content of soluble CD44var in sera of 6 healthy donors was determined by two different ELISAs. In one test VFF-7, while in the other VFF-18 was used as coating antibody. In both cases, a recombinant soluble CD44variant (exon v3–v10) produced in CHO cells served as control. In the average, the VFF-18 ELISA showed 3.5 times higher values as compared to the VFF-7 ELISA. This means that compared to the recombinant protein. The soluble CD44var occurring in serum is better recognized by VFF-18 than by VFF-7.

TABLE 6

| Donor | VFF-7 ng/ml | VFF-18 ng/ml | VFF-18/VFF-7 |
|---|---|---|---|
| 1 | 18.2 | 75.9 | 4.17 |
| 2 | 32.1 | 85.5 | 2.66 |
| 3 | 22.4 | 87.6 | 3.91 |
| 4 | 27.7 | 91.6 | 3.31 |
| 5 | 26.8 | 98.3 | 3.67 |
| 6 | 95.4 | 332 | 3.48 |
| mean value | | | 3.53 |
| SD | | | 0.52 |
| CV% | | | 14.9% |

References

Barbas C F, Björling E, Chiodi F, Dunlop N, Cababa D, Jones T M, Zebedee S L, Persson M A A, Nara P L, Norrby E, Burton D R. Recombinant human Fab fragments neutralize human type 1 immunodeficiency virus in vitro. *Proc. Natl. Acad. Sci. U. S. A.* 89: 9339–9343 (1992).

Breitz H B, Weiden P L, Vanderheyden J-L, Appelbaum J W, Bjom M J, Fer M F, Wolf S B, Ratcliff B A, Seiler C A, Foisie D C, Fisher D R, SchroffR W, Fritzberg A R, Abrams P G. Clinical experience with rhenium-186-labeled monoclonal antibodies for radioimmunotherapy: results of phase I trials. *J Nucl. Med* 33: 1099–1112 (1992).

Catty, D., Raykundalia, C. ELISA and related immunoassays. In: Catty, D (Hrsg). *Antibodies Vol. II.* IRL Press Oxford (1989), 97–152, pp105–109.

Catty, D., Murphy, G. Immunoassays using radiolabels. In: Catty, D (Hrsg). *Antibodies Vol. II.* IRL Press Oxford (1989), pp77–96.

Chatal J-F, Saccavini J-C, Gestin J-F, Theddrez P, Curtet C, Kremer M, Guerreau D, Nolibé D, Fumoleau P, Guillard Y. Biodistribution of indium-111-labeled OC 125 monoclonal antibody intraperitoneally injected into patients operated on for ovarian carcinomas. *Cancer Res.* 49: 3087–3094 (1989).

Chaudhary V K, Batra J K, Galdo M G, Willingham M C, Fitzgerald D J, Pastan I. A rapid method of cloning functional variable-region antibody genes in *Escherichia coli* as single-chain immunotoxins. *Proc. Natl. Acad. Sci. U. S. A.* 87: 1066 (1990).

Colcher D, Esteban J, Carrasquillo J A, Sugarbaker P, Reynolds J C, Bryant G, Larson S M, Schlom J. Complementation of intracavitary and intravenous administration of a monoclonal antibody (B72.3) in patients with carcinoma. *Cancer Res.* 47: 4218–4224 (1987).

Coloma M J, Hastings A, Wims L A, Morrison S L. Novel vectors for the expression of antibody molecules using variable regions generated by polymerase chain reaction. *J Immmunol. Methods* 152: 89–104 (1992).

Friedmann P N, McAndrew S J, Gawlak S L, Chace D, Trail P A, Brown J P, Siegall C B. BR96 sFv-PE40, a potent single-chain immunotoxin that selectively kills carcinoma cells. *Cancer Res.* 53: 334–339 (1993).

Goodwin D A. A new appoach to the problem of targeting specific monoclonal antibodies to human tumors using anti-hapten chimeric antibodies. *J Nucl. Med Biol.* 16: 645 (1989).

Günthert, U., Hofmann, M., Rudy, W., Reber, S., Zöller, M., Haußmann, I., Matzku, S., Wenzel, A., Ponta, H., and Herrlich, P. A new variant of glycoprotein CD44 confers metastatic potential to rat carcinoma cells. *Cell* 65: 13–24 (1991).

Guesdon, J. I., Ternynck, T., Avrameas, S. *J Histochem. Cytochem.* 27: 1131 (1979).

Güssow D, Seemann G. Humanization of monoclonal antibodies. *Methods Enzymol.* 203: 99–121 (1991):

Heider, K.-H., Hofmann, M., Horst, E., van den Berg, F., Ponta, H., Herrlich, P., and Pals, S. T. A human homologue of the rat metastasis-associated variant of CD44 is expressed in colorectal carcinomas and adenomatous polyps. *J Cell Biol.* 120: 227–233 (1993a).

Heider, K-H., Dammrich, J., Skroch-Angel, P., Mtiller-Hermelink, H-K., Vollmers, H-P., Herrlich, P., and Ponta, H. Differential expression of CD44splice variants in intestinal- and diffuse-type human gastric carcinomas and normal gastric mucosa. *Cancer Res.* 53: 4197–4203 (1993b).

Hofmann, M., Rudy, W., Zöller, M., Tolg, C., Ponta, H., Herrlich P., and Günthert, U. CD44splice variants confer metastatic behavior in rats: homologous sequences are expressed in human tumor cell lines. *Cancer Res.* 51: 5292–5297 (1991).

Johnson, G. D. Immunofluorescence. In: Catty, D (Hrsg). *Antibodies Vol. II.* IRL Press Oxford (1989), 179–200, pp180–189.

Johnson S, Bird R E. Construction of single-chain derivatives of monoclonal antibodies and their production in *Escherichia coli*. *Methods Enzymol.* 203: 88–98 (1991).

Kearney, J. F., Radbruch A., Liesegang B., Rajewski K. A new mouse myeloma cell line that has lost imunoglobulin expression but permits construction of antibody-secreting hybrid cell lines. *J Immunol.* 123: 1548 (1979).

Keenan A M, Weinstein J N, Carrasquillo J A, Bunn P A, Reynolds J C, Foon K A et al. Immunolymphoscintigraphy and the dose dependence of $^{111}$In-labeled T101 monoclonal antibody in patients with cutaneous T-cell lymphoma. *Cancer Res.* 47: 6093–6099 (1987).

Köhler, G., Milstein, C. Continous culture of fused cells secreting antibody of predefined specifity. *Nature* 265: 495 (1975)

Koopman, G., Heider, K.-H., Horts, E., Adolf, G. R., van den Berg, F., Ponta, H., Herrlich, P., Pals, S. T. Activated human lymphocytes and aggressive Non-Hodgkin's lymphomas express a homologue of the rat metastasis-associated variant of CD44. *J Exp. Med* 177: 897–904 (1993).

Kreitman R J, Hansen H J, Jones A L, FitzGerald D J P, Goldenberg D M, Pastan I. Pseudomonas exotoxin-based immunotoxins containing the antibody LL2 or LL2-Fab' induce regression of subcutaneous human B-cell lymphoma in mice. *Cancer Res.* 53: 819–825 (1993).

Larson S M, Cheung N-K V, Leibel S A. Radioisotope Conjugates. In: DeVita V T, Hellman S, Rosenberg S A (Eds.). Biologic therapy of cancer. J. B. Lippincott Comp., Philadelphia, 496–511 (1991).

Mulshine J L, Magnani J L, Linnoila R I: Applications of monoclonal antibodies in the treatment of solid tumors. In: DeVita V T, Hellman S, Rosenberg S A (Eds.). Biologic therapy of cancer. J. B. Lippincott Comp., Philadelphia, pp563–588 (1991).

Nesbit M, Fu Z F, McDonald-Smith J, Steplewski Z, Curtis P J. Production of a functional monoclonal antibody recognizing human colorectal carcinoma cells from a baculovirus expression system. *J Immunol. Methods* 151: 201–208 (1992).

Perkins A C, Pimm M V. A role for gamma scintigraphy in cancer immunology and immunotherapy. *Eur. J Nucl. Med* 19; 1054–1063 (1992).

Press O W, Eary J F, Badger C C, Martin P J, Appelbaum F R, Levy R, Miller R, Brown S, Nelp W B, Krohn K A, Fisher D, DeSantes K, Porter B, Kidd P, Thomas E D, Bernstein I D. Treatment of refractory Non-Hodgkin's lymphoma with radiolabeled MB-1 (anti-CD37) antibody. *J Clin. Oncol.* 7:1027–1038 (1989).

Rudy, W., Hofmann, M., Schwartz-Albiez, R., Zöller, M., Heider, K.-H., Ponta, H., Herrlich, P. The two major CD44 proteins expressed on a metastatic rat tumor cell line are derived from different splice variants: Each one individually suffices to confer metastatic behaviour. *Cancer Res.* 53: 1262–1268 (1993).

Schrappe M, Bumol T F, Apelgren L D, Briggs S L, Koppel G A, Markowitz D D, Mueller B M, Reisfeld R A. Long-term growth suppression of human glioma xenografts by chemo-immunoconjugates of 4-desacetylvinblastine-3-carboxyhydrazide and monoclonal antibody 9.2.27. *Cancer Res.* 52: 3838–3844 (1992).

Screaton, G. R., Bell, M. V., Jackson, D. G., Comelis, F. B., Gerth, U., and Bell, J. I. Genomic structure of DNA encoding the lymphocyte homing receptor CD44 reveals at least 12 alternatively spliced exons. *Proc. Natl. Acad. Sci. U. S. A.* 89: 12160–12164 (1992).

Sears H F, Mattis J, Herlyn D, Häyry P, Atkinson B, Ernst C, Steplewski Z, Koprowski H. Phase-I clinical trial of monoclonal antibody in treatment of gastrointestinal tumours. *Lancet* 1982 (1): 762–765 (1982).

Seiter, S., Arch, R., Reber, S., Komitowski, D., Hofmann, M., Ponta, H:, Herrlich, P., Matzku, S., Zöller, M. Prevention of tumor metastasis formation by anti-variant CD44. *J Exp. Med.* 177: 443–455 (1993).

Senter P D, Schreiber G J, Hirschberg D L, Ashe S A, Hellström K E, Hellström I. Enhancement of the in vitro and in vivo antitumor activities of phosphorylated mitomycin C and etoposide derivatives by monoclonal antibody-alkaline phosphatase conjugates. *Cancer Res.* 49: 5789–5792 (1989).

Shin S-U, Morrison S L. Production and properties of chimeric antibody molecules. *Methods Enzymol.* 178: 459–476 (1989).

Smith, D. B., Johnson, K .S. Single-step purification of polypetides expressed in *Escherichia coli* as fusions with glutathione 5-transferase. *Gene* 67: 31–40 (1988).

Srivastava S C (Hrsg). Radiolabeled monoclonal antibodies for imaging and therapy. *Life Sciences Series A* 152, Plenum N.Y. (1988).

Tölg, C., Hofmann, M., Herrlich, P., and Ponta, H. Splicing choice from ten variant exons establishes CD44 variability. *Nucleic Acids. Res.* 21: 1225–1229 (1993).

Theuer C P, Kreitman R J, FitzGerald D J, Pastan I. Immunotoxins made with a recombinant form of pseudomonas exotoxin A that do not require proteolysis for activity. *Cancer Res.* 53: 340–347 (1993).

Thompson C H, Stacker S-A, Salehi N, Lichtenstein M, Leyden M J, Andrews J T. Immunoscintigraphy for detection of lymph node metastases from breast cancer. *Lancet* 1984 (2): 1245–1247 (1984).

Thomas G D, Dykes P W, Bradwell A R. Antibodies for tumour immunodetection and methods for antibody radiolabeling. In: Catty D (Ed.). Antibodies. IRL Press Oxford, (1989), pp223–244.

Vitetta E S, Thorpe P E. Immunotoxins. In: DeVita V T, Hellman S, Rosenberg S A (Eds.). Biologic therapy of cancer. J. B. Lippincott Comp., Philadelphia, 482–495 (1991)

Vitetta E S, Stone M, Amlot P, Fay J, May R, Till M, Newman J, Clark P, Collins R, Cunningham D, Ghetie V, Uhr J W, Thorpe P E. Phase I immunotoxin trial in patients with B-cell lymphoma. *Cancer Res.* 51: 4052–4058 (1991).

Wang S-M, Chern J-W, Yeh M-Y, Ng J C, Tung E, Roffler S R. Specific activation of glucuronide prodrugs by antibody-targeted enzyme conjugates for cancer therapy. *Cancer Res.* 52: 4484–4491 (1992).

Weiner L M, O'Dwyer J, Kitson J, Comis R L, Frankel A E, Bauer R J, Kopnrad M S, Groves E S. Phase I evaluation of an anti-breast carcinoma monoclonal antibody 260F9-recombinant ricin A chain immunoconjugate. *Cancer Res.* 49: 4062–4067 (1989).

Wielenga, V. J. M., Heider, K.-H., Offerhaus, G. J. A., Adolf, G. R., van den Berg, F. M., Ponta, H., Herrlich, P., Pals, S.T. Expression of CD44variant proteins in human colorectal cancer is related to tumor progression. *Cancer Res.* 53: 4754–4756 (1993).

Winter, G., Griffith, A. D., Hawkins, R. E., Hoogenboom, H. R. Making antibodies by phage display technology. *Ann. Rev. Immunol.* 12, 433–455 (1994).

We claim:

1. Antibody VFF-18 produced by the hybridoma cell line with the accession number DSM AC2174.

2. A hybridoma cell line with the accession number DSM ACC2174.

3. An antibody molecule derived from antibody VFF-18, obtainable by chemical or enzymatic modification of antibody VFF-18 wherein said antibody molecule retains the antigen binding specificity of antibody VFF-18.

4. An antibody molecule according to claim 3 wherein said antibody molecule is a fragment of antibody VFF-18 which retains the antigen binding specificity of antibody VFF-18.

5. An antibody molecule according to claim 4 wherein said antibody molecule is a Fab fragment or F(ab')$_2$ fragment.

6. An antibody molecule according to claim 3 wherein said antibody molecule is linked to another molecule.

7. An antibody molecule according to claim 6 wherein said other molecule is a polypeptide.

8. An antibody molecule according to any one of claims 3 to 5 wherein said antibody molecule is linked to a radioactive isotope.

9. A recombinant antibody molecule having the idiotype of antibody VFF-18.

10. A recombinant antibody molecule according to claim 9 wherein said recombinant antibody molecule is a chimeric, humanised, or single chain antibody molecule, or an antibody molecule generated by chain shuffling, wherein said antibody molecule substantially retains the antigen binding specificity of antibody VFF-18.

11. A recombinant antibody molecule according to claim 9 or 10 wherein said antibody molecule is linked to another molecule or to a radioactive isotope.

12. An antibody molecule recognizing the same epitope as antibody VFF-18.

13. An in vitro diagnostic method for detecting expression of the variant exon v6 of the CD44 gene, comprising:
   (a) contacting an antibody according to claim 1 or an antibody molecule according to any one of claims 3 to 12 to a tissue sample or liquid obtained from a human or animal body such that said antibody or said antibody molecule binds to an epitope encoded by the variant exon v6 of the CD44 gene if the epitope is contained in the tissue sample or liquid;
   (b) washing the tissue sample or liquid; and
   (c) detecting if said antibody or said antibody molecule bound to the epitope.

14. A diagnostic method according to claim 13 wherein said diagnostic method is an enzyme-linked immunoassay or a radioimmunoassay.

15. A diagnostic method according to claim 13 wherein said diagnostic method is an immunohistochemical method.

16. A pharmaceutical composition comprising antibody VFF-18 or an antibody molecule according to any one of claims 3–7, 9 or 10.

17. A diagnostic reagent comprising antibody VFF-18 or an antibody molecule according to any one of claims 3–7, 9 or 10, wherein said diagnostic reagent binds in vivo to tumor cell cells that express variant exon v6 of the CD44 gene.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
    (A) LENGTH: 27 base pairs
    (B) TYPE: nucleotide
    (C) STRANDEDNESS: single stranded
    (D) TOPOLOGY: linear (ii) MOLECULE TYPE: Other nucleic acid
    (A) DESCRIPTION:  /desc = "PCR Primer"

(xi) SEQUENCE DESCRIPTION: SEQ ID NO:1:

CAGGCTGGGA GCCAAATGAA GAAAATG                                       27

(2) INFORMATION FOR SEQ ID NO:2:

(i) SEQUENCE CHARACTERSTICS:
    (A) LENGTH: 30 base pairs
    (B) TYPE: nucleotide
    (C) STRANDEDNESS: single stranded
    (D) TOPOLOGY: linear (ii) MOLECULE TYPE: Other nucleic acid
    (A) DESCRIPTION:  /desc = "PCR Primer"

(xi) SEQUENCE DESCRIPTION: SEQ ID NO:2:

TGATAAGGAA CGATTGACAT TAGAGTTGGA                                    30

(2) INFORMATION FOR SEQ ID NO:3:

(i) SEQUENCE CHARACTERISTICS:
    (A) LENGTH: 14 amino acids
    (B) TYPE: amino acid
    (C) STRANDEDNESS: single stranded
    (D) TOPOLOGY: linear (ii) MOLECULE TYPE: Peptide (xi) SEQUENCE DESCRIPTION: SEQ ID NO:3:

Lys Trp Phe Glu Asn Glu Trp Gln Gly Lys Asn Pro Pro Thr
1               5                   10

(2) INFORMATION FOR SEQ ID NO:4:

(i) SEQUENCE CHARACTERSTICS:
    (A) LENGTH: 14 amino acids
    (B) TYPE: amino acid
    (C) STRANDEDNESS: single stranded
    (D) TOPOLOGY: linear (ii) MOLECULE TYPE: Peptide (xi) SEQUENCE DESCRIPTION: SEQ ID NO:4:

Gln Trp Phe Gly Asn Arg Trp His Glu Gly Tyr Arg Gln Thr
1               5                   10

(2) INFORMATION FOR SEQ ID NO:5:

(i) SEQUENCE CHARACTERSTICS:
    (A) LENGTH: 42 amino acids
    (B) TYPE: amino acid
    (C) STRANDEDNESS: single stranded
    (D) TOPOLOGY: linear -continued

```
    (ii) MOLECULE TYPE: Peptide (xi) SEQUENCE DESCRIPTION: SEQ ID NO:5:

Trp Ala Asp Pro Asn Ser Thr Thr Glu Glu Ala Ala Thr Gln Lys Glu
1               5                   10                  15

Lys Trp Phe Glu Asn Glu Trp Gln Gly Lys Asn Pro Pro Thr Pro Ser
                20                  25                  30

Glu Asp Ser His Val Thr Glu Gly Thr Thr
            35                  40

(2) INFORMATION FOR SEQ ID NO:6:

(i) SEQUENCE CHARACTERSITICS:
        (A) LENGTH: 43 amino acids
        (B) TYPE: amino acids
        (C) STRANDEDNESS: single stranded
        (D) TOPOLOGY: linear (ii) MOLECULE TYPE: Peptide (xi) SEQUENCE DESCRIPTION: SEQ ID NO:6:

Gln Ala Thr Pro Ser Ser Thr Thr Glu Glu Thr Ala Thr Gln Lys Glu
1               5                   10                  15

Gln Trp Phe Gly Asn Arg Trp His Glu Gly Tyr Arg Gln Thr Pro Arg
                20                  25                  30

Glu Asp Ser His Ser Thr Thr Gly Thr Ala Ala
            35                  40
```